United States Patent
Choi et al.

(10) Patent No.: US 9,482,658 B2
(45) Date of Patent: Nov. 1, 2016

(54) TEST SYSTEM AND METHOD FOR DETERMINING THERMAL EFFECTS OF TISSUE ABLATION ON AN EX VIVO TISSUE

(71) Applicant: Ohio University, Athens, OH (US)

(72) Inventors: Junghun Choi, Athens, OH (US); Liang Chen, Athens, OH (US)

(73) Assignee: Ohio University, Athens, OH (US)

( * ) Notice: Subject to any disclaimer, the term of this patent is extended or adjusted under 35 U.S.C. 154(b) by 415 days.

(21) Appl. No.: 14/224,494

(22) Filed: Mar. 25, 2014

(65) Prior Publication Data

US 2014/0286374 A1 Sep. 25, 2014

Related U.S. Application Data

(60) Provisional application No. 61/804,881, filed on Mar. 25, 2013.

(51) Int. Cl.
  G09B 23/28 (2006.01)
  G01N 33/483 (2006.01)
  A61B 18/00 (2006.01)

(52) U.S. Cl.
  CPC . *G01N 33/4833* (2013.01); *A61B 2018/00577* (2013.01); *A61B 2018/00595* (2013.01)

(58) Field of Classification Search
  USPC ....... 434/262, 267, 270, 272, 295, 296, 297; 606/32, 37, 41, 42
  See application file for complete search history.

(56) References Cited

U.S. PATENT DOCUMENTS

| | | | |
|---|---|---|---|
| 6,632,193 B1 | 10/2003 | Davison et al. | |
| 7,993,140 B2 * | 8/2011 | Sakezles | G09B 23/306 434/267 |
| 8,425,234 B2 * | 4/2013 | Sakezles | G09B 23/28 434/274 |
| 8,801,438 B2 * | 8/2014 | Sakezles | G09B 23/30 434/274 |
| 8,870,576 B2 * | 10/2014 | Millon | 434/267 |

(Continued)

FOREIGN PATENT DOCUMENTS

AU 2012203166 A1 12/2012
EP 1571969 A2 9/2005

(Continued)

OTHER PUBLICATIONS

Bujanda, L., Cosme, A., Gil, I., and Arenas-Mirave, J.I., 2010, "Malignant Colorectal Polyps," World J Gastroenterol, 16 (25), pp. 3103-3111.

(Continued)

*Primary Examiner* — Kurt Fernstrom
(74) *Attorney, Agent, or Firm* — Wood Herron & Evans LLP (57) ABSTRACT

A test system and method for determining thermal effects of tissue ablation on an ex vivo tissue includes a power generator, a grounding patch, and a material block configured to emulate an electrical property of a patient. The power generator electrically connects to an electrode to generate an electrical current in the electrode. The grounding patch electrically connects to the power generator, and the material block electrically connects to the grounding patch. Furthermore, the material block includes an ex vivo tissue patch configured to emulate an in vivo tissue of the patient. As such, selectively engaging the electrode to the ex vivo tissue patch electrically connects the electrode to the grounding patch through the material block for electrocauterizing the ex vivo tissue patch.

20 Claims, 5 Drawing Sheets

(56) References Cited

U.S. PATENT DOCUMENTS

| | | | |
|---|---|---|---|
| 8,961,190 B2* | 2/2015 | Hart | G09B 23/30 434/267 |
| 2002/0198523 A1 | 12/2002 | Behl | |
| 2003/0084907 A1 | 5/2003 | Pacek et al. | |
| 2007/0203485 A1 | 8/2007 | Keppel | |
| 2007/0239156 A1 | 10/2007 | Palanker et al. | |
| 2012/0150170 A1 | 6/2012 | Buysse et al. | |
| 2013/0059280 A1* | 3/2013 | Haverich | C12N 5/00 434/272 |
| 2013/0108999 A1* | 5/2013 | Gillies | G09B 23/303 434/272 |
| 2015/0037776 A1* | 2/2015 | Redaelli | G09B 23/30 434/272 |

FOREIGN PATENT DOCUMENTS

| | | |
|---|---|---|
| EP | 2314244 A1 | 4/2011 |
| EP | 2469699 A2 | 6/2012 |
| WO | 2010120944 A2 | 10/2010 |
| WO | 2010142438 A2 | 12/2010 |
| WO | 2013019702 A1 | 2/2013 |

OTHER PUBLICATIONS

American Cancer Society, 2011, "Cancer Facts and Figures 2011," Atlanta, GA: American Cancer Society.

Williams, C. and Teague, R., 1973, "Colonoscopy," Gut, 14(12), pp. 990-1003.

Winawer, S.J., Zauber, A.G., Ho, M.N., O'Brien, M.J., Gottlieb, L.S., Sternberg, S.S., Waye, J.D., Schapiro, M., Bond, J.H., and Panish, J.F., 1993, "Prevention of Colorectal Cancer by Colonoscopic Polypectomy, The National Polyp Study Workgroup," N Engl J Med, 329(27), pp. 1977-1981.

Ginsberg, G.G., 2008, "Risks of Colonoscopy and Polypectomy," Techniques in Gastrointestinal Endoscopy, 10, pp. 7-13.

Massarweh, N.N., Cosgriff, N., and Slakey, D.P., 2006, "Electrosurgery: History, Principles, and Current and Future Uses," J Am Coll Surg, 202(3), pp. 520-530.

Gilbert, D.A., DiMarino, A.J., Jensen, D.M., Katon, R., Kimmey, M.B., Laine, L.A., MacFadyen, B.V., Michaletz-Onody,. P.A., and Zuckerman, G., 1992, "Status Evaluation: Hot Biopsy Forceps, American Society for Gastrointestinal Endoscopy. Technology Assessment Committee," Gastrointest Endosc, 38(6), pp. 753-756.

Morris, M.L, Tucker, R.D., Baron, T.H., and Song, L.M.W.K., 2009, "Electrosurgery in Gastrointestinal Endoscopy: Principles to Practice," Am J Gastroenterol, 104(6), pp. 1563-1574.

Jia-ke, C., Li-gen, L., Quan-wen, G., Xiao-peng, S., Hai-jun, Z., Zhi-yong, S., Zhi-qiang, W., and Cai, Z., 2009, "Establishment of Soft-Tissue-Injury Model of High-voltage Electrical Burn and Observation of its Pathological Changes," Burns, 35(8), pp. 1158-1164.

Fyock, C.J., Draganov P.V., 2010, "Colonscopic Polypectomy amd Associated Techniques," World J Gastroenterol, 16 (29), pp. 3630-3637.

Kedia, P., Waye, J.D., 2011, :Routine and Advanced Polypectomy Techniques., Curr Gastroenterol Rep, 13, pp. 506-511.

Zauber, A.G., Winawer, S. J., O'Brien, M.J., Lansdorp-Vogelaar, I., van Ballegooijen, M., Hankey, B.F., Shi, W., Bond, J.H., Schapiro, M., Panish, J.F., Stewart E. T., Waye, J.D., 2012, "Colonoscopic Polypectomy and Long-Term Prevention of Colorectal-Cancer Deaths," N Engl J Med, 366(8), pp. 687-696.

Vancaille, T.G., 1998, "Active Electrode Monitoring: How to prevent unintentional thermal injury associated with monopolar electrosurgery at laparoscopy," Surgical Endoscopy, 12, pp. 1009-1012.

Khaled, A.R. and Vafai, K., 2003, "The Role of Porous Media in Modeling Flow and Heat Transfer in Biological Tissues," International Journal of Heat and Mass Transfer, 46, pp. 4989-5003

Haines, D.E., 1991, "Determinants of Lesion Size During Radiofrequency Catheter Ablation: The Role of Electrode-Tissue Contact Pressure and Duration of Energy Delivery," Journal of Cardiovascular Electrophysiology, 2, pp. 509-515.

Chinpairoj, S., Feldman, M.D., Saunders, J.C., and Thaler, E.R., 2001, "A Comparison of Monopolar Electrosurgery to a New Multipolar Electrosurgical System in a Rat Model," Laryngoscope, 111(2), pp. 213-217.

Dodde, R.E., Gee, J.S. Geiger, J.D., and Shih, A.J., 2012, "Monopolar Electrosurgical Thermal Management for Minimizing Tissue Damage," IEEE Trans Biomed Eng, 59(1), pp. 167-173.

Saltzman, J.R., Thiesen, A., and Liu, J.J., 2010, "Determination of Optimal Monopolar Coagulation Settings for Upper GI Bleeding in a Pig Model," Gastrointest Endosc, 72(4), pp. 796-801.

Chino, A., Karasawa, T., Uragami, N., Endo, Y., Takahashi, H., and Fujita, R., 2004, "A Comparison of Depth of Tissue Injury Caused by Different Modes of Electrosurgical Current in a Pig Colon Model," Gastrointest Endosc, 59(3), pp. 374-379.

Goulet, C.J., DiSario, J.A., Emerson, L., Hilden, K., Holubkov, R., and Fang, J.C., 2007, "In vivo Evaluation of Argon Plasma Coagulation in a Porcine Model," Gastrointest Endosc, 65(3), pp. 457-462.

Hon, S.S.F., Ng, S.S.M., Lee, J.F.Y., Li, J.C.M., and Lo, A.W.I., 2010, "In vitro porcine training model for colonic endoscopic submucosal dissection: an inexpensive and safe way to acquire a complex endoscopic technique." Surg Endosc, 24(10), pp. 2439-2443.

Tanaka, S., Morita, Y., Fujita, T., Wakahara, C., Ikeda, A., Toyonaga, T., and Azuma, T., 2012, "Ex vivo pig training model for esophageal endoscopic submucosal dissection (ESD) for endoscopists with experience in gastric ESD," Surg Endosc, 26(6), pp. 1579-1586.

Parra-Blanco, A., Arnau, M.R., Nicolás-Pérez, D., Gimeno-García, A.Z., González, N., Díaz-Acosta, J.A., Jiménez, A., and Quintero, E., 2010, "Endoscopic submucosal dissection training with pig models in a Western country," World J Gastroenterol, 16(23), pp. 2895-2900.

Vázquez-Sequeiros, E., de Miguel, D.B., Olcina, J.R.F., Martin, J.A.G., Garcia, M., Lucas, D.J., Garrido, E., González, C., Blanco, A.P., Arnau, M.R., Buenadicha, A., Vicente, V.M., de Argila, C.M., and Milicua, J.M., 2009, "Training model for teaching endoscopic submucosal dissection of gastric tumors." Rev Esp Enferm Dig, 101(8), pp. 546-552.

Tanimoto, M.A., Torres-Villalobos, G., Fujita, R., Santillan-Doherty, P., Albores-Saavedra, J., Gutierrez, G., Martin-del Campo, L.A., Bravo-Reyna, C., Villanueva, O., Villalobos, J.J., Uribe, M., and Valdovinos, M.A., 2010, "Endoscopic submucosal dissection in dogs in a World Gastroenterology Organisation training center," World J Gastroenterol, 16 (14), pp. 1759-1764.

Avwioro, G., 2011, "Histochemical Uses of Haematoxylin—A Review," Journal of Pharmacy and Clinical Sciences, 1 (5), pp. 24-34.

Jovanovic, I., Caro, C., Neumann, H., Lux, A., Kuester, D., Fry, L.C., Malfertheiner, P., and Mönkemüller, K., 2011, "The Submucosal Cushion does not Improve the Histologic Evaluation of Adenomatous Colon Polyps Resected by Snare Polypectomy," Clin Gastroenterol Hepatol, 9(10), pp. 910-913.

Chrambach, A., Rodbard, D., 1971, "Polyacrylamide Gel Electrophoresis," Science, New Series, 172(3982), pp. 440-451.

Robert, R., Chen, L. Choi J. Drozek, D., 2012, "Variable Assessment for Design of Monopolar Hot Biopsy Forceps," Minneapolis, MN, USA; Design of Medical Device Conference, pp. 1.

Cobb, W.S., Heniford, B.T. Sigmon, L.B., Hasan, R., Simms, C., Kercher K.W., Matthews B.D., 2004, "Colonoscopic Perforations: Incidence, Management, and Outcomes," The American Surgeon, 70, pp. 750-758.

Lüning, T.H., Keemer-Gels, M.E., Barendregt, W.B., Tan, A.C.I.T. L., Rosman, C., 2007, "Colonoscopic perforations: a review of 30, 366 patients," Surg Endosc, 21, pp. 994-997.

Iqbal, C.W., Cullinane, D.C., Schiller H.J., Sawyer M.D., Zietlow S.P., Farley, D.R., 2008, "Surgical Management and Outcomes of 165 Colonscopic Perforations from a Single Institution," Arch Surg, 143(7) pp. 701-707.

Teoh, A.Y.B., Poon, C. M., Lee, J.F.Y., Leong, H.T., Ng, S. S. M., Sung, J.J.Y., Lau, J.J.W.S., 2009, "Outcomes and Predictors of Mortality and Stoma Formation in Surgical Management of Colonoscopic Perforations," Arch Surg, 144 (1), pp. 9-13.

(56) References Cited

OTHER PUBLICATIONS

Lohsiriwat, V., 2010, "Colonoscopic perforation: Incidence, risk factors, management and outcome," World J Gastroenterol, 16(4), pp. 425-430.

La Torre M., Velluti, F., Giulio E.D., Ziparo, V., La Torre, F., 2011, "Promptness of diagnoses is the main prognostic factor after colonoscopic perforation." Colorectal Disease, The Association of Coloprotology of Great Britain and Ireland, 14, pp. 23-26.

Yahagi, N., Heuhaus, H., Schumacher, B. Neugebauer, A., Kaehler, G.F., Schenk, M., Fischer, K., :Comparison of standard endoscopic submucousal dissection(ESD) versus an optimized ESD technique for the colon: an animal study, Endoscopy, 41, pp. 340-345.

Zhang, X-L., Qu, J-H, Tang, P., Yang, Y-S., 2012, "Feasibility study of secure closure of gastric fundus perforation using over-the-scope clips in a dog model," J of Gastroent and Hepatology, 27, 1200-1204.

Bok, G.H., Cho, J.Y., 2012, "ESD Hands-On Course Using Ex Vivo and In Vivo Models in South Korea," Clin Endos, 45, pp. 358-361.

Sedlack, R.E., Baron, T.H., Downing, S.M., Schwartz, A.J., 2007, "Validation of a Colonoscopy Simulation Model for Skills Assessment," Am J Gastroenterol 102, pp. 64-74.

Holder, D.S., Khan, A., 1994, "Use of polyacrylamide gels in a saline-filled tank to determine the linearity of the Sheffield Mark 1 electrical impedance tomography (EIT) system in measuring impedance disturbances," Physiol. Meas., 15, pp. A45-A50.

Kasting, G.B., Merritt, E.W., Keister, J.C., 1988, "An in Vitro Method for Studying the Iontophoretic Enhancement of Drug Transport Through Skin," J of Membrane Science, 35, pp. 137-159.

Kasting, G.B., Bowman, L.A., 1990, "DC Electrical Properties of Frozen, Excised Human Skin," Pharmaceutical Research, 7(2), pp. 134-143.

Panteris, V., Haringsma, J., Kuipers, E.J., 2009, "Colonoscopy perforation rate, mechanisms and outcome: from diagnostic to therapeutic colonoscopy," Endoscopy, 41(11) pp. 941-051.

Vilos, G. Jul. 2010, "How to do electrosurgery Safely. Out Patient Surgery," 1(7) from http://www.outpatientsurgery.net/issues/2000/07/how-to-do-electrosurgery-safely.

Pliquett, F., Pliquett, U., 1996, "Passive Electrical Properties of Human Stratum Corneum in vitro Depending on Time after Separation," Biophysical Chemistry, 58, pp. 205-210.

van der Sluis, F.J., Loffeld, R.J., Engel, A.F., 2011, "Outcome of surgery for colonoscopic perforation," Colorectal Disease, The Association of Coloproctology of Great Britain and Ireland, 14, pp. e187-s190.

Lewis, G.K., Jr., Lewis, G.K., Sr., Olbricht, W., 2008, "Cost-Effective broad-band electrical impedance spectroscopy measurement circuit and signal analysis for piezo-materials and ultrasound transducers," Meas Sci Technol, 19(10), pp. 1-13.

Gabriel, S., Lau, R.W., Gabriel, C., 1996, "The dielectric properties of biological tissues: II. Measurements in the frequency range 10 Hz to 20 GHz," Phys. Med. Biol., 41, pp. 2251-2269.

Walsh, J.T., Flotte, T.J., Deutsch, T.F., 1989, "Er: YAG Laser Ablation of Tissue: Effect of Pulse Duration and Tissue Type on Thermal Damage," Lasers in Surgery and Medicine, 9, pp. 314-326.

\* cited by examiner

TEST SYSTEM AND METHOD FOR DETERMINING THERMAL EFFECTS OF TISSUE ABLATION ON AN EX VIVO TISSUE

CROSS-REFERENCE TO RELATED APPLICATION

This application claims the priority of Application Ser. No. 61/804,881 filed Mar. 25, 2013 (pending), the disclosure of which is hereby incorporated by reference herein.

TECHNICAL FIELD

The present invention relates generally to a test system and method for determining thermal effects of tissue ablation on a tissue, and more particularly, to a test system and method for effectively testing and comparing the thermal effects of tissue ablation by a variety of models and/or devices.

BACKGROUND

One of the most common and dangerous electrosurgical procedures is monopolar electrosurgery for removing polyps, such as colorectal polyps, with an endoscope and hot biopsy forceps. While such biopsy forceps are widely used for removing polyps that may be associated with colorectal cancer, successfully removing polyps with minimal damage to a patient's tissue requires significant training to properly inspect an ablation region for thermal damage. For example, a practitioner, such as a doctor, nurse, or other trained medical professional, typically visually inspects the ablation region for growth of a white peripheral crest to indicate a depth of the thermal effects into the tissue caused by the ablation of the polyp.

On the one hand, visually overestimating the depth of the thermal effects of the ablation may lead the practitioner to incorrectly conclude that the polyp has been completely removed by the biopsy forceps and, in turn, may fail to fully remove the polyp. On the other hand, visually underestimating the depth of the thermal effects of the ablation may cause the practitioner to inadvertently damage the patient's tissue resulting in potentially life-threatening complications. Such underestimations are further complicated by the fact that these complications may include a delayed perforation of the patient's tissue after the patient as left the practitioner and is no longer surrounded by trained medical professionals for immediate treatment.

Due to the difficulty associated with estimating the thermal effects of ablation, particularly in vivo with the patient, a variety of theoretical models and devices have been developed to aid in measuring and/or predicting the depth of ablation. For example, one theoretical model attempts to correlate duration and output power of an electrosurgical device to the patient's tissue to the depth of ablation. Another theoretical model focuses on thermal management of the biopsy forceps for limiting the effective heat field in the patient's tissue via simulated computer models. However, further development of these models and devices are, to some extent, limited by an inability to accurately and precisely compare the effectiveness of these developments.

There is a need for a test system and method of determining the thermal effects of tissue ablation on an ex vivo tissue that addresses present challenges and characteristics such as those discussed above.

SUMMARY

An exemplary embodiment of a test system for determining thermal effects of tissue ablation on an ex vivo tissue patch includes a power generator, a grounding patch, and a material block configured for emulating an electrical property of a patient. The power generator is electrically connected to an electrode and configured to generate an electrical current in the electrode. The grounding patch is electrically connected to the power generator, and the material block is electrically connected to the grounding patch. The material block includes the ex vivo tissue patch configured to emulate an in vivo tissue of the patient. Accordingly, selectively engaging the electrode to said ex vivo tissue patch electrically connects the electrode to the grounding patch through the material block for electrocauterizing the ex vivo tissue patch.

An exemplary embodiment of a material block for emulating an electrical property of a patient includes a polyacrylamide gel base and an ex vivo tissue patch. The ex vivo tissue patch is directly connected to the polyacrylamide gel base and configured to emulate an in vivo tissue of the patient. As such, the polyacrylamide gel base and the ex vivo tissue patch are configured to collectively emulate an electrical property of the patient.

In use, an exemplary method for determining thermal effects of tissue ablation on an ex vivo tissue patch includes connecting an ex vivo tissue patch to a polyacrylamide gel base to form a material block configured to emulate an in vivo tissue of a patient and an electrical property of the patient. The method also includes electrocauterizing the ex vivo tissue patch with an electrode and burning a hole into a portion of the ex vivo tissue patch. Furthermore, the method includes measuring the electrical property of the material block.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

DETAILED DESCRIPTION

Figure 1:
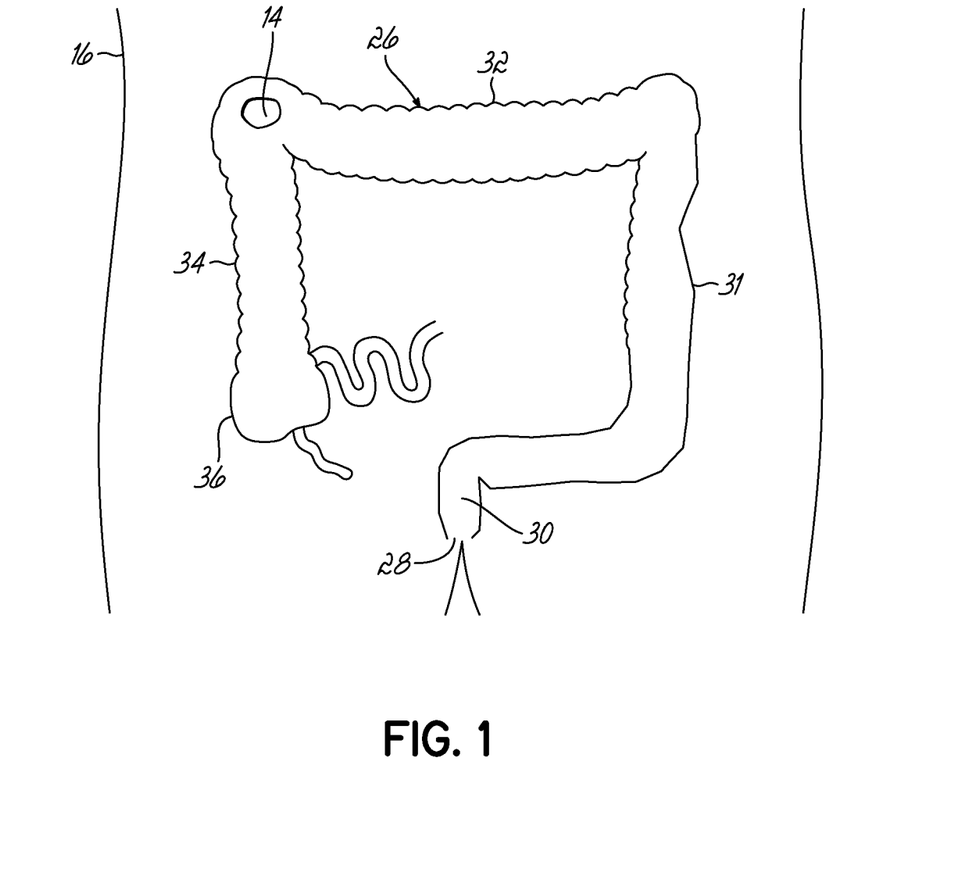
FIG. 1 is a schematic view of a colon of a patient.
Figure 2:
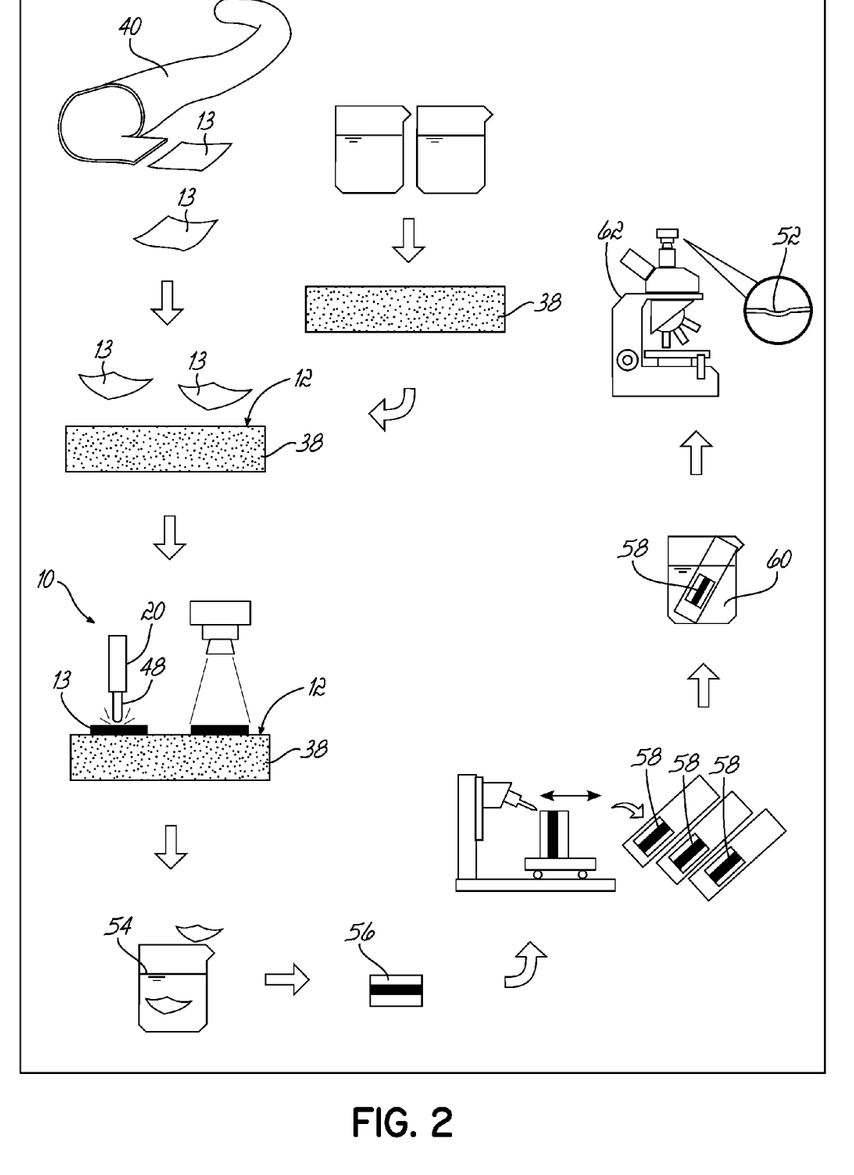
FIG. 2 is a diagrammatic view of an exemplary method of determining thermal effects of tissue ablation on an ex vivo tissue patch.
Figure 3:
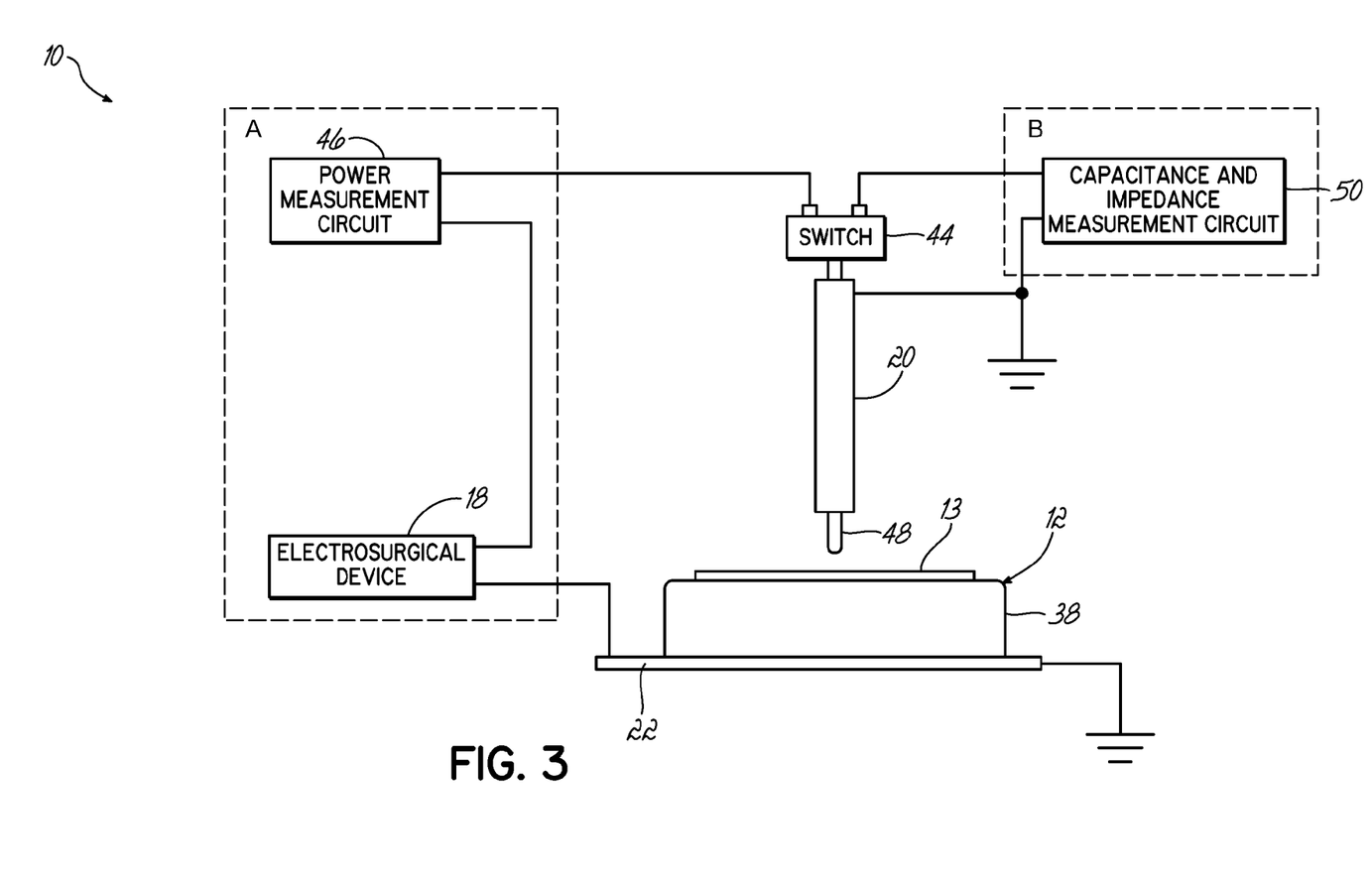
FIG. 3 is a diagrammatic view of an exemplary test assembly for performing the method of FIG. 2.

With reference to FIGS. 1-3, a test assembly 10 includes a material block 12 having an ex vivo tissue patch 13 for emulating an in vivo tissue 14 of a patient 16. The test assembly 10 further includes a power generator 18, such as the electrosurgical device 18, electrically connected to an electrode 20 and a grounding patch 22. With reference to the term "emulate" described herein, the material block 12 emulates the patient 16 by having physical and/or electrical properties that correlate to the physical and/or electrical properties of the patient 16. According to an exemplary embodiment, the physical and/or electrical properties of the material block 12 may be similar or generally the same as the patient 16. Alternatively, the physical and/or electrical properties of the material block 12 may be different from the patient 16, so long as a user, such as a doctor, nurse, lab technician, or similarly trained professional, can correlate these properties to the patient 16. As such, the material block 12 is electrically connected to the grounding patch 22, and the electrode 20 is brought into selective engagement with the ex vivo tissue patch 13 to electrocauterize the ex vivo tissue patch 13 and ablate a portion of the ex vivo tissue patch 13. Generally, the test assembly 10 and method described herein are described as an exemplary test to compare one or more devices for performing an ablation. Alternatively or in addition, the test may also be useful for teaching, training, and testing new or used equipment.

According to an exemplary embodiment, the material block 12 is configured to emulate a portion of a colon 26 of the patient 16. FIG. 1 shows a schematic view of the patient 16 and the colon 26. The colon 26 generally extends from the anus 28 and rectum 30 to the descending colon 31 and upward to the transverse colon 32. From the transverse colon 32, the colon 26 extends downward toward the ascending colon 34 and cecum 36. Typically, the colon 26 is inspected, such as during a colonoscopy, with an endoscope (not shown) having a hot biopsy forceps (not shown) configured for ablating a polyp via electrocauterization. While testing and training with an endoscope and biopsy forceps in vivo is often useful, the difficulties associated with estimating depth of tissue ablation in vivo require significant training. For this reason, the test assembly 10 and material block 12 having an ex vivo tissue patch 13 may be used to develop devices, including endoscopes and biopsy forceps, such as those discussed in U.S. patent application Ser. No. 14/203, 990 filed on Mar. 11, 2014, the disclosure of which is hereby incorporated by reference in its entirety.

The colon 26 includes a wall having several layers between an interior of the colon 26 and an exterior of the colon 26. The layers of the wall, from the interior to the exterior, include the mucosa, the submucosa, an inner layer of the muscularis propria, and an outer layer of the muscularis propria. Thus, in the event of an in vivo ablation via a biopsy forceps, the initial layer to be electrocauterized is the mucosa. Of course, deeper ablations may extend through the remaining layers and, in the event of perforation, effectively burn through the entire wall of the colon 26. According to an exemplary embodiment, the material block 12 is configured to emulate the wall of the colon 26 during ablation. However, it will be appreciated that the material block 12 may be configured to replicate other tissues of the patient 16. For this reason, the invention described herein is not intended to be limited to emulating colon tissue of the patient 16.

FIG. 2 schematically shows a method, or test model, of generally forming the material block 12, electrocauterizing the ex vivo tissue patch 13, and preparing the electrocauterized ex vivo tissue patch 13. The material block 12 includes the ex vivo tissue patch 13 and a gel base 38. An exemplary ex vivo tissue patch 13 is formed from a porcine colon 40; however, it will be appreciated that any colon that emulates the patient colon 26 may be so used. The porcine colon 40 is rinsed with phosphate-buffered saline (PBS) and then fixed with 70% ethanol for storage at −20° C. within a freezer (not shown). Prior to testing, the porcine colon 40 is warmed to room temperature and rinsed with distilled water to remove the ethanol. Once the ethanol is removed, the porcine colon 40 is cut into one or more ex vivo tissue patches 13, which, according to an exemplary embodiment, are each sized to be a 1 inch by 1 inch square.

The gel base 38 is formed from a polyacrylamide gel (PAG) having a 15% resolution gel formula with the reagents listed below in Table 1 and generally includes acyrlamide, bisacrylamide, tris(hydroxymethyl)amino methane (Tris-HCl Buffer), ammonium persulfate (APS), tetramethylethylenediamine (TEMED), and distilled degas water in the amounts shown for 60 ml of gel.

TABLE 1

Gel Reagents List

| Reagent | Description | Quantity (60 ml of Gel) |
| --- | --- | --- |
| Acrylaminde/Bisacrylaminde | 40% Solution | 22.5 ml |
| Tris—HCl Buffer | 1.5M, pH 8.8 | 15 ml |
| APS | white to yellowish crystals | 60 mg |
| TEMED | solution | 50-60 µl |
| Distilled degas water | | 22.5 ml |

The acyrlamide/bisacrylamide solution and Tris-HCl buffer are mixed together and pooled into a frame, such as a plastic mold. The APS is weighted and dissolved in distilled water and added into the frame with the other materials. To begin consolidating the gel, TEMED is added into the frame and, after about 20 minutes, the gel base 38 is formed. The gel base 38 may then be stored in cold distilled water until needed for testing with the ex vivo tissue patch 13. Please note, however, that APS is not stable and should be prepared for each gel base 38. By way of example, other volumes of gel bases 38 with relative quantities of these materials are shown in Table 2.

TABLE 2

Detailed Gel Formula for 60 ml and 80 ml of gel

| Reagent | Amount for 60 ml of Gel | Amount for 80 ml of Gel |
| --- | --- | --- |
| Acrylaminde/Bisacrylaminde | 22.5 ml | 30 ml |
| Tris—HCl Buffer | 15 ml | 20 ml |
| APS | 60 mg | 80 mg |
| TEMED | 50-60 µl | 80 µl |
| Distilled degas water | 22.5 ml | 30 ml |

In order to quantify the emulation of the electrical property of the gel base 38, which may also include the ex vivo tissue patch 13 attached thereto, an electrical impedance of the gel block was measured under radio-frequency and included the measurements shown in Table 3. Notably, the cauterization electrode 20 was also included in the following measurements for improved accuracy.

TABLE 3

Electrical Impedance Measurement Parameters

| Parameter | Value |
| --- | --- |
| Experiment Type | Frequency Sweep, Control Voltage |
| DC potential | 0 mV |
| AC potential | 2000 mV |
| Frequency (lower bound) | 50 Hz |

TABLE 3-continued

Electrical Impedance Measurement Parameters

| Parameter | Value |
|---|---|
| Frequency (upper bound) | 300 kHz |
| Frequency Sweep Type | Log |
| Frequency Step | Decade |
| Frequency Interval | 50 |

The ex vivo tissue patch 13 is connected to the gel base 38 to form the material block 12. The material block 12 is then electrically connected to the grounding patch 22, which may also be referred to herein as a returning electrode, of the test assembly 10 shown in FIG. 2 and FIG. 3. The test assembly 10 generally includes a cauterizing portion A and an electrical measurement portion B, both of which are electrically connected to the electrode 20 via a switch 44 for isolating the cauterizing and electrical measurement portions A, B.

The cauterizing portion A includes the electrosurgical device 18 operatively connected to a CPU (not shown) and a power measurement circuit 46. The electrosurgical device 18 provides power to the electrode 20 via the power measurement circuit 46 and is controlled by the CPU for precise cauterization control. The power measurement circuit 46 may be monitored during use to verify the power being delivered to the electrode 20. Notably, the switch 44 isolates the electrical measurement portion B from the cauterizing portion A so that power and, more particularly electrical current, is delivered to a head 48, or tip, of the electrode 20 rather than the measurement portion B.

The measurement portion B includes an electrical measurement circuit 50, which according to an exemplary embodiment is a capacitance and impedance measurement circuit 50. The electrical measurement circuit 50 is operatively connected to a CPU (not shown) for collecting electrical values detected before cauterization and after cauterization. For example, the electrical measurement circuit 50 and CPU will determine the capacitance values by counting the discharging/charging time with constant voltage/current. According to an exemplary embodiment, the electrode 20 and head 48 are in the form of a one-foot RF cable, rather than a biopsy forceps and endoscope. However, it will be appreciated that such a biopsy forceps, or other equivalent electrode, may be used as described herein.

During an exemplary test of the test assembly 10, an electrical property of the material block 12 is collected via the electrical measurement circuit 50, such as capacitance and/or impedance. Then, the head 48 selectively engages the ex vivo tissue patch 13 to form one or more holes 52 (see FIG. 4A) in the ex vivo tissue patch 13. Once the hole 52 (see FIG. 4A) if formed, the electrical property of the material block 12 is again collected via the electrical measurement circuit 50. An exemplary set of electrocauterization test parameters are shown below in Table 4.

TABLE 4

Electrocauterization Test Parameters

| Parameter | Unit | Values | Count |
|---|---|---|---|
| Power | watt | 30, 50, 80 | 3 |
| Duration | second | 0.5, 1.5, 3.0 | 3 |
| Contacting Area | | low, high | 2 |

Figure 4A:
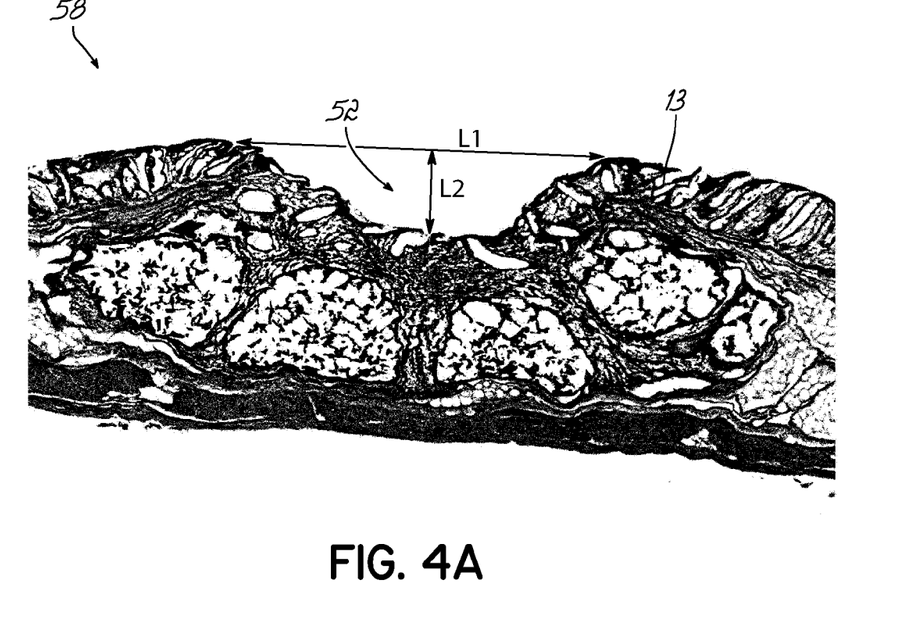
FIG. 4A is a cross-section view of the ex vivo tissue patch of FIG. 2 after removing a portion of the ex vivo tissue patch with the test assembly of FIG. 3.
Figure 4B:
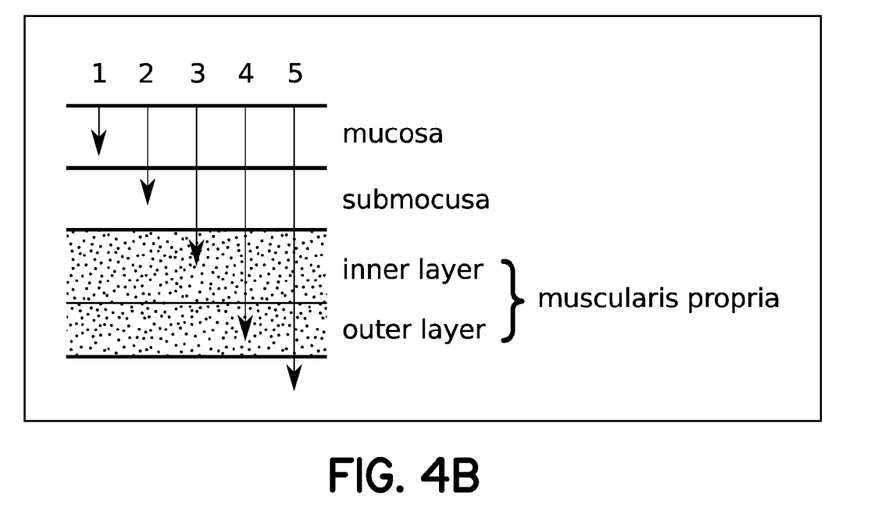
FIG. 4B is a chart showing an exemplary grading scale for indicating a depth of ablation on the ex vivo tissue patch of FIG. 4A.

With respect to FIG. 2 and FIGS. 4A-4B, photographs are taken of the holes 52 after the electrocauterization. The ex vivo tissue patch 13 is removed from the gel base 38 for undergoing histological analysis for quantifying the size of each hole 52. Generally, the analysis requires dehydration of the ex vivo tissue patch 13, embedding the ex vivo tissue patch 13 in paraffin, slicing the paraffin to form cross-sectional slices of the ex vivo tissue patch 13, staining the cross-sectional slices, and inspecting the cross-sectional slices with a microscope 62. The following will provide additional details for this analysis.

With the ex vivo tissue patch 13 removed from the gel base 38, the ex vivo tissue patch 13 is manipulated with ethanol and xylene for dehydration 54. The following steps outline the dehydration process in Table 5. Once dehydrated, each ex vivo tissue patch 13 is submerged and embedded in melted paraffin until the paraffin hardens into paraffin blocks 56. Each paraffin block 56 is sliced from 6 to 12 times to define 6 to 12 10 μm slides 58 of the ex vivo tissue patch 13.

TABLE 5

Sample Dehydration Procedure

| Step | Reagent | Time |
|---|---|---|
| 1 | 70% Ethanol | Overnight |
| 2 | 70% Ethanol | 2.0 hours |
| 3 | 70% Ethanol | 1.5-2.0 hours |
| 4 | 70% Ethanol | 30 min (repeat 3 times) |
| 5 | Xylene | 20 min (repeat 3 times) |
| 6 | Paraffin I | 1.0-2.0 hours |
| 7 | Paraffin II | Overnight |
| 8 | Paraffin II | 30 min |

Preferably, the slides 58 are stained for viewing details of the cross-sections of the ex vivo tissue patch 13. According to an exemplary embodiment, each slide 58 is stained with haematoxylin and eosin (H&E) 60. Staining the slides 58 with H&E 60 includes hydrating each slice of the ex vivo tissue patch 13, applying the H&E 60, and dehydrating each slide 58 again for photographing and storage. The following Table 6 outlines the successive operations for staining each slide 58.

TABLE 6

H&E Staining Procedure (including hydration and dehydraton)

| Operation | Time |
|---|---|
| Submerge slides in Xylene I, II, and III | 5 minutes (each) |
| Submerge slides in 100% Ethanol I and II | 5 minutes (each) |
| Submerge slides in 95% Ethanol | 5 minutes |
| Submerge slides in 70% Ethanol | 5 minutes |
| Wash slides in distilled water | 3 minutes |
| Submerge slides in Haematoxylin | 2 minutes |
| Wash slides in circulating bath with tap water | 20 minutes |
| Wash slides in distilled water | 3 minutes |
| Submerge slides in 70% Ethanol | 3 minutes |
| Submerge slides in Eosin | 30 seconds |
| Submerge slides in 95% Ethanol | 3 minutes |
| Submerge slides in 100% Ethanol I, II, and III | 3 minutes (each) |
| Submerge slides in Xylene I, II, and III | 3 minutes (each) |

FIG. 4A shows an exemplary photograph of a slide 58 defining the hole 52 within the ex vivo tissue patch 13. Notably, the hole 52 has a diameter L1 and a depth L2. The diameter L1 and depth L2, taken in conjunction with the other slides 58, may be used to calculate the volume of the hole 52 formed in the ex vivo tissue patch 13. It will be appreciated that the volume may be calculated using known mathematical estimations, such as a volume of a spherical cap, or may be scanned for measurement. In any case, the depth L2 may then be correlated to an injury grade shown in FIG. 4B. For example, a depth through the mucosa correlates to an injury grade 1, whereas, a depth through the inner layer of the muscularis propria correlates to an injury grade 4.

Figure 5:
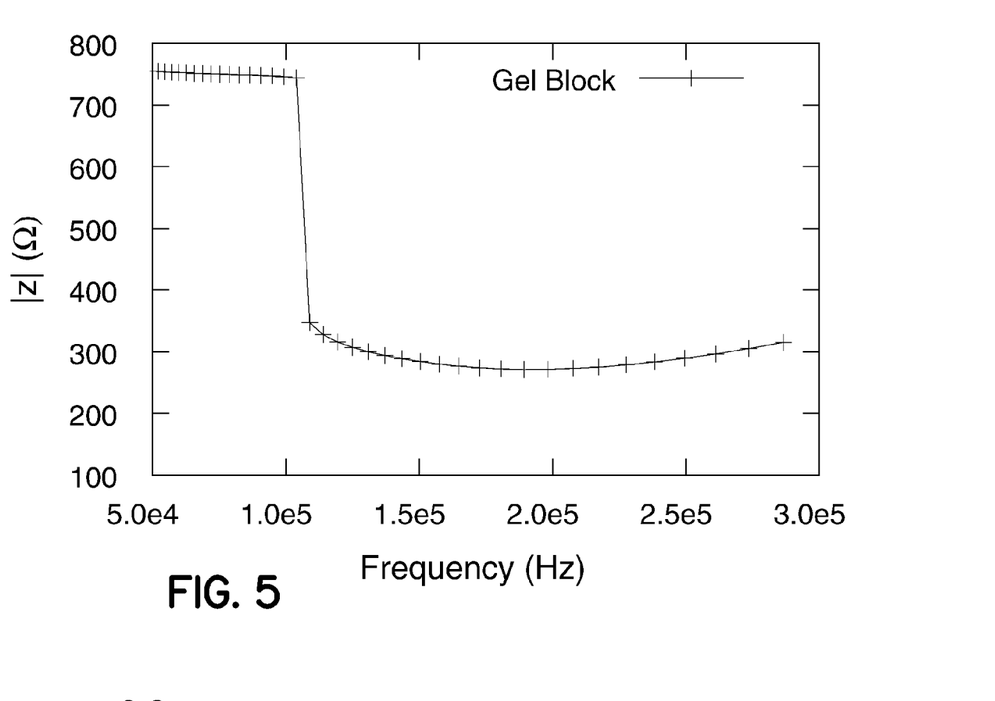
FIG. 5 is a chart showing an electrical impedance value of an exemplary material block including a polyacrylamide gel.
Figure 6:
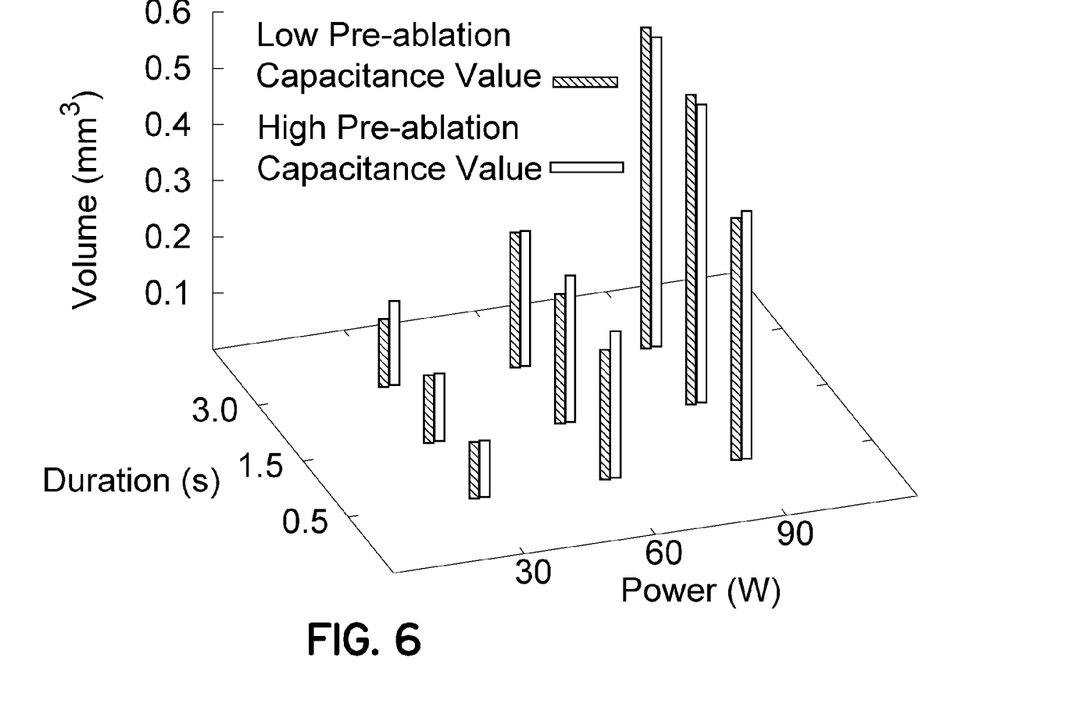
FIG. 6 is a chart showing an electrical capacitance value of an exemplary material block including a polyacrylamide gel.

By understanding the measurements, such as the depth and the volume, of the hole 52, the electrical values, such as the capacitance and impedance, can be compared to the resulting hole 52 and correlated for comparing other treatments ex vivo or predicting injury grades of a hot biopsy forceps in vivo. By way of example, FIG. 5 shows impedance values and capacitance values taken during cauterization with the test assembly 10 of FIG. 3. With respect to FIG. 5, the material block 12 had an impedance value of 300Ω at a frequency range of 150 kHz to 300 kHz. Notably, at relatively low-frequency, the material block 12 has a relatively stable impedance value and, as such, emulates the similar electrical impedance values of in vivo tissue 14. Furthermore, FIG. 6 shows a capacitance value correlated to the volume of the hole 52 measured from the slides 58. In this way, the capacitance values measured before and after ablating a portion of the ex vivo tissue 13 can be used to indicate to a user the size of the hole 52 formed during during cauterization.

While the present invention has been illustrated by the description of one or more embodiments thereof, and while the embodiments have been described in considerable detail, they are not intended to restrict or in any way limit the scope of the appended claims to such detail. For example, the references to the colonoscopy procedure and the polyp tissue are not intended to limit the invention. It will be appreciated that the invention may be used in relation to any electrosurgical procedure and on any patient tissue. The various features shown and described herein may be used alone or in any combination. Additional advantages and modifications will readily appear to those skilled in the art. The invention in its broader aspects is therefore not limited to the specific details, representative device and method and illustrative examples shown and described. Accordingly, departures may be from such details without departing from the scope of the general inventive concept.

What is claimed is:

1. A test system for determining thermal effects of tissue ablation on an ex vivo tissue patch, comprises;
    a power generator electrically connected to an electrode, said power generator configured to generate an electrical current in the electrode;
    a grounding patch electrically connected to said power generator;
    a material block electrically connected to the grounding patch and configured to emulate an electrical property of a patient, said material block including said ex vivo tissue patch configured to emulate an in vivo tissue of the patient,
    wherein selectively engaging said electrode to said ex vivo tissue patch electrically connects said electrode to said grounding patch through said material block for electrocauterizing said ex vivo tissue patch.

2. The test system of claim 1, wherein said material block further comprises a polyacrylamide gel base positioned electrically between said ex vivo tissue patch and said grounding patch.

3. The test system of claim 2, wherein said ex vivo tissue patch is directly connected to said polyacrylamide gel base to form said material block.

4. The test system of claim 2, wherein said polyacrylamide gel base further comprises acyrlamide, bisacrylamide, tris(hydroxymethyl)amino methane, ammonium persulfate, tetramethylethylenediamine, and distilled degas water.

5. The test system of claim 1, wherein said ex vivo tissue patch is formed from a porcine colon.

6. The test system of claim 1 further comprising:
    an electrical measurement circuit selectively and electrically connected to said electrode for measuring the electrical property of said material block.

7. The test system of claim 6 further comprising:
    an electrical switch configured to selectively and electrically disconnect said electrical measurement circuit from said electrode.

8. The test system of claim 6, wherein said electrical property is at least one of capacitance and impedance.

9. The test system of claim 1, wherein said power generator is an electrosurgical device power generator.

10. A material block for emulating an electrical property of a patient, comprising;
    a polyacrylamide gel base; and
    an ex vivo tissue patch directly connected to said polyacrylamide gel base, said ex vivo tissue patch configured to emulate an in vivo tissue of the patient,
    wherein said polyacrylamide gel base and said ex vivo tissue patch are configured to collectively emulate the electrical property of the patient.

11. The material block of claim 10, wherein said polyacrylamide gel base further comprises acyrlamide, bisacrylamide, tris (hydroxymethyl) amino methane, ammonium persulfate, tetramethylethylenediamine, and distilled degas water.

12. The material block of claim 10, wherein said ex vivo tissue patch is formed from a porcine colon.

13. A method of determining thermal effects of tissue ablation on an ex vivo tissue patch, comprises;
    connecting the ex vivo tissue patch to a polyacrylamide gel base to form a material block configured to emulate an in vivo tissue of a patient and an electrical property of the patient;
    electrocauterizing the ex vivo tissue patch with an electrode and burning a hole into a portion of the ex vivo tissue patch; and
    measuring the electrical property of the material block.

14. The method of claim 13 further comprising:
    cutting a porcine colon to form the ex vivo tissue patch.

15. The method of claim 13 further comprising:
    mixing acyrlamide, bisacrylamide, tris (hydroxymethyl) amino methane, ammonium persulfate, tetramethylethylenediamine, and distilled degas water into a mixed solution; and
    forming the mixed solution into the polyacrylamide gel base.

16. The method of claim 13 further comprising:
    dehydrating the ex vivo tissue patch having the hole therein.

17. The method of claim 16 further comprising:
    embedding the dehydrated ex vivo tissue patch into a paraffin block.

18. The method of claim 17 further comprising:
    slicing the paraffin block with the embedded ex vivo tissue patch to form a plurality of slides, each slide containing a cross-section of the ex vivo tissue patch.

19. The method of claim 18 further comprising:
staining the plurality of slides for viewing the cross-section of the ex vivo tissue patch.

20. The method of claim 13 further comprising:
estimating a depth of the hole; and
correlating the depth of the hole to the measured electrical property.

* * * * *